United States Patent [19]
Bremmer

[11] Patent Number: 4,579,654
[45] Date of Patent: Apr. 1, 1986

[54] APPARATUS FOR THE ANAEROBIC FERMENTATION OF ORGANIC WASTE MATERIAL SUCH AS LIQUID MANURE

[75] Inventor: Hendrik M. Bremmer, Oisterwijk, Netherlands

[73] Assignee: Corite Investments Ltd., St. Peter Port, Channel Islands

[21] Appl. No.: 506,778

[22] Filed: Jun. 22, 1983

[30] Foreign Application Priority Data

Jun. 25, 1982 [NL] Netherlands .......................... 8202584

[51] Int. Cl.⁴ .......................... C02F 11/04; C12P 5/02; C12M 1/02
[52] U.S. Cl. .................... 210/180; 210/188; 210/218; 210/256; 210/603; 48/111; 48/197 A; 435/167; 435/316; 435/801
[58] Field of Search ...................... 210/180, 188, 242.1, 210/603, 605, 608, 613, 614, 218, 256; 48/197 A, 111; 435/167, 801, 316

[56] References Cited

U.S. PATENT DOCUMENTS

| | | | |
|---|---|---|---|
| 2,195,408 | 4/1940 | Downes | 210/188 |
| 3,933,628 | 1/1976 | Varani | 210/12 |
| 3,981,803 | 9/1976 | Coulthard | 210/180 |
| 4,082,672 | 4/1978 | Petroski | 210/218 |
| 4,100,023 | 7/1978 | McDonald | 48/197 A |
| 4,318,993 | 3/1982 | Ghosh et al. | 48/197 A |

FOREIGN PATENT DOCUMENTS

| | | | |
|---|---|---|---|
| 1048146 | 12/1953 | France . | |
| 1215772 | 4/1960 | France . | |
| 2409305 | 6/1979 | France . | |
| 1452781 | 10/1976 | United Kingdom | 210/605 |

Primary Examiner—Benoit Castel
Attorney, Agent, or Firm—Hopgood, Calimafde, Kalil, Blaustein & Judlowe

[57] ABSTRACT

An apparatus for the anaerobic digestion of organic waste material such as manure in liquid condition include bringing the waste material in an acidification space with a roof collecting gas generated thereby and one or more openings below said roof giving access from said space to a methane fermentation space so that the gas below the roof pushes the liquid to said latter space. A discharge of gas from below said roof to the outside allows liquid to flow back through said openings into the acidification space. Below said roof there may be a separate wall defining a hydrolysis space, into which the waste material is fed before flowing to the acidification space. The whole of the device or considerable parts of the walls and ducts thereof may be made of flexible gastight material so as to be easily folded or wound up for transport to the site of use so as to be inflatable to sustain its operating shape by a higher than atmospheric pressure of the gas therein.

10 Claims, 5 Drawing Figures 4,579,654

APPARATUS FOR THE ANAEROBIC FERMENTATION OF ORGANIC WASTE MATERIAL SUCH AS LIQUID MANURE

BACKGROUND OF THE INVENTION

The invention relates to a device for the anaerobic fermentation of organic waste material such as manure in a substantially liquid condition.

For the anaerobic fermentation of organic waste material such as liquid manure it is necessary to transfer this material first of all into more simple and soluble compositions by acidification, which compositions are suitable to be fermented by methane bacteria while generating methane and carbon dioxide gas (biogas). In particular when the waste material comprises solid organic components, a hydrolysis is first of all necessary, which transfers such components into soluble substances. Hydrolysis and acidification may take place in the same space mainly by the same types of bacteria.

For smaller plants, for instance on farms, experiments have been made with biogas devices which were relatively expensive to obtain such fermentation. Such devices have several objections, both as to the costs as to the maintaining of the process in an active state and therein hydrolysis and acidification often took place in the same space as the methane fermentation, although this has disadvantages for an efficient performance of the several processes, the yield of biogas was relatively small and a relatively considerable part of said gas was necessary for the energy required by the device itself for pumping, mixing and stirring.

OBJECTS AND SUMMARY OF THE INVENTION

The present invention aims at improving this and at providing an apparatus which is very efficient, requires low costs and energy and is simple in mounting, structure, operation and maintenance.

The invention characterized in that the waste material in a liquid condition adapted to be pumped easily is introduced in an acidifying space, in which the gas generated therein is entrapped and collected below a roofing of said space separating said space from a bordering methane fermentation space, the pressure of the gas collected below said roofing pressing said liquid from said acidifying space to said methane fermentation space through an opening in the lower part of the wall of said roofing below the gas collecting space therein, the gas being discharged from below said roofing.

This given a good separation between on the one hand acidification (if desired combined with hydrolysis) and methane fermentation on the other hand, the gas generation during said acidification and hydrolysis influencing the flow of the liquid to the methane fermentation space, so that the liquid is pushed by said gas to the methane fermentation space to a considerable extent only after said acidification (and hydrolysis) have proceeded to a considerable extent. This is so because said gas generation is a result of and is dependent on the amount in which hydrolysis and acidification have taken place. This gives in total a shorter residence period of the liquid to be treated in the device, which gives for a certain volume of the device a high capacity thereof.

As such it is known, at least for large devices, to separate acidification (and hydrolysis) from methane fermentation and to have these processes take place in different reactor spaces.

Preferably the invention is realized in such a way that the gas from below said roofing is at least in part introduced into the liquid in the methane fermentation space. If this is done gradually, this gives a good and not too strong stirring of the liquid in the methane fermentation space. In many cases it is however, preferable not to do this exclusively gradually, but periodically and by sudden blows of discharge. This has several advantages. Often a rather dense and closed floating layer of material in a somewhat scum-like condition is formed on the liquid in the methane fermentation space and this is by such periodic and sudden blows broken up adequately by the gas and disintegrated. The warmer gas heats the liquid. Moreover the gas pressure and gas quantity below the roofing is thereby decreased suddenly, so that liquid from the methane fermentation space flows back into the acidification space giving a good mixing in said space and causing acidification and hydrolysis to take place more completely and avoiding too much settling of solid particles in the lower zone of the methane fermentation space. The returning liquid is mainly liquid of which the acidification is not yet entirely completed, so that finally acidification takes place more completely. This is thus obtained in a simple manner without supply of energy as the gas generated itself gives this energy. Moreover this means that after such a short period of strong stirring the fermentation space has a longer period of quiet conditions, which promotes a good course of the fermentation.

Even if the gas from below the roofing is not fed to the methane fermentation space but is discharged from the device because it consists for the greater part of carbon dioxide, so that it is often not desired to mix a too high quantity thereof with the methane from the methane fermentation space, this periodical and blowing discharge as described is preferable in view of the advantages stated even if in that case they are only in part applicable.

The invention also allows easy means to have hydrolysis and acidification take place in separate spaces, which improves the yield further, as will be described below.

A device for the anaerobic digestion of organic waste material such as manure in a substantially liquid condition is according to the invention characterized in that it comprises a digestion container, in which in the lower part a tunnel is provided, into which the supply of liquid to be treated opens, said tunnel having a roof which, together with part of its upstanding sidewalls form a collecting space for gas with their lower and inner surface parts, said tunnel having an opening near its lower part giving liquid communication to a methane formentation space extending alongside and at least in part above said tunnel.

Such a device has several advantages, in part as described above, and moreover it may entirely or to a considerable part be made of flexible, foldable or windable material so that it may easily be transported and mounted and be particularly suited for operating under a somewhat increased pressure, so that the gas leaves the device at a pressure which is adequate for further use, said higher pressure maintaining the flexible walls of the device in the desired "blown-up" shape. This also gives easily a considerable storing space for the gas. By such flexible walls they will easily change their shape somewhat depending on pressures and amount of liquid therein so that by movements of such flexible walls sticking of solid parts to said walls is counteracted.

BRIEF DESCRIPTION OF THE DRAWINGS

The above mentioned and further features and advantages will appear in more detail from the following description of the annexed drawings showing two preferred embodiments of a device according to the invention. In said drawings.

DESCRIPTION OF THE PREFERRED EMBODIMENTS

Figure 1:
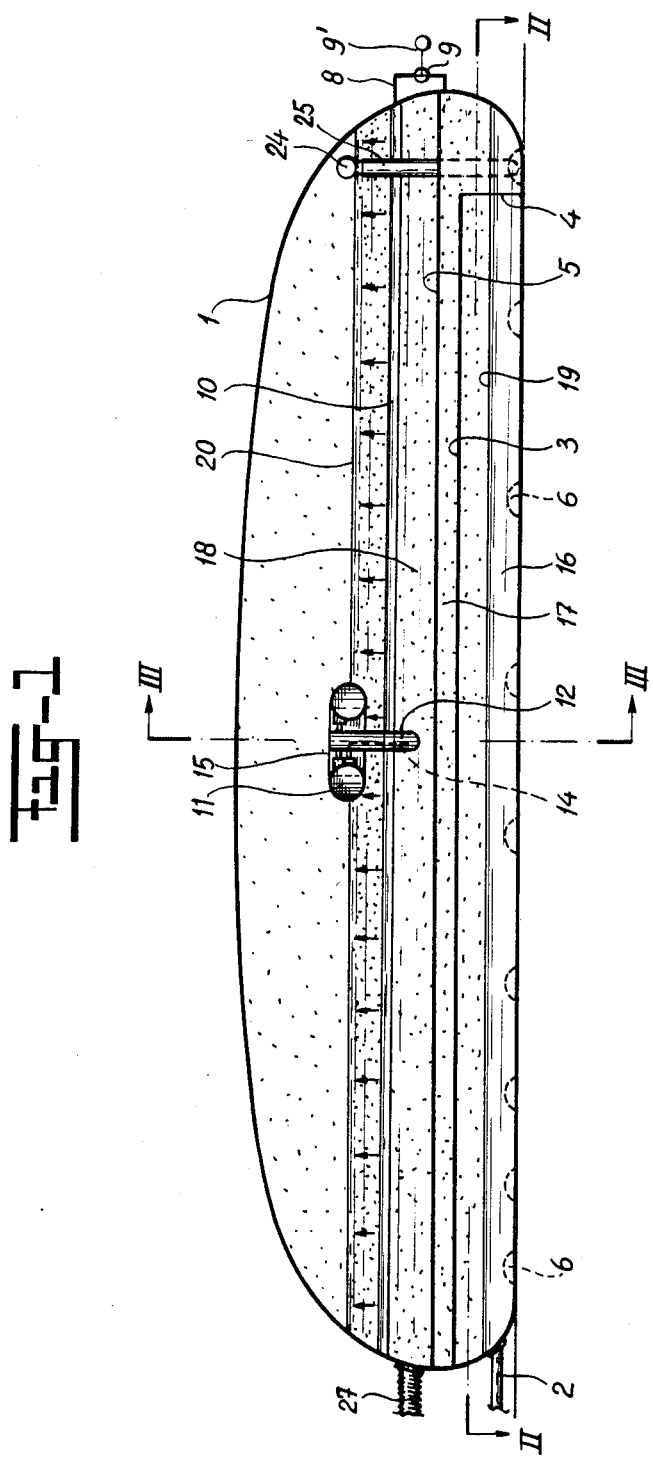
FIG. 1 is a vertical longitudinal section through such a device.
Figure 2:
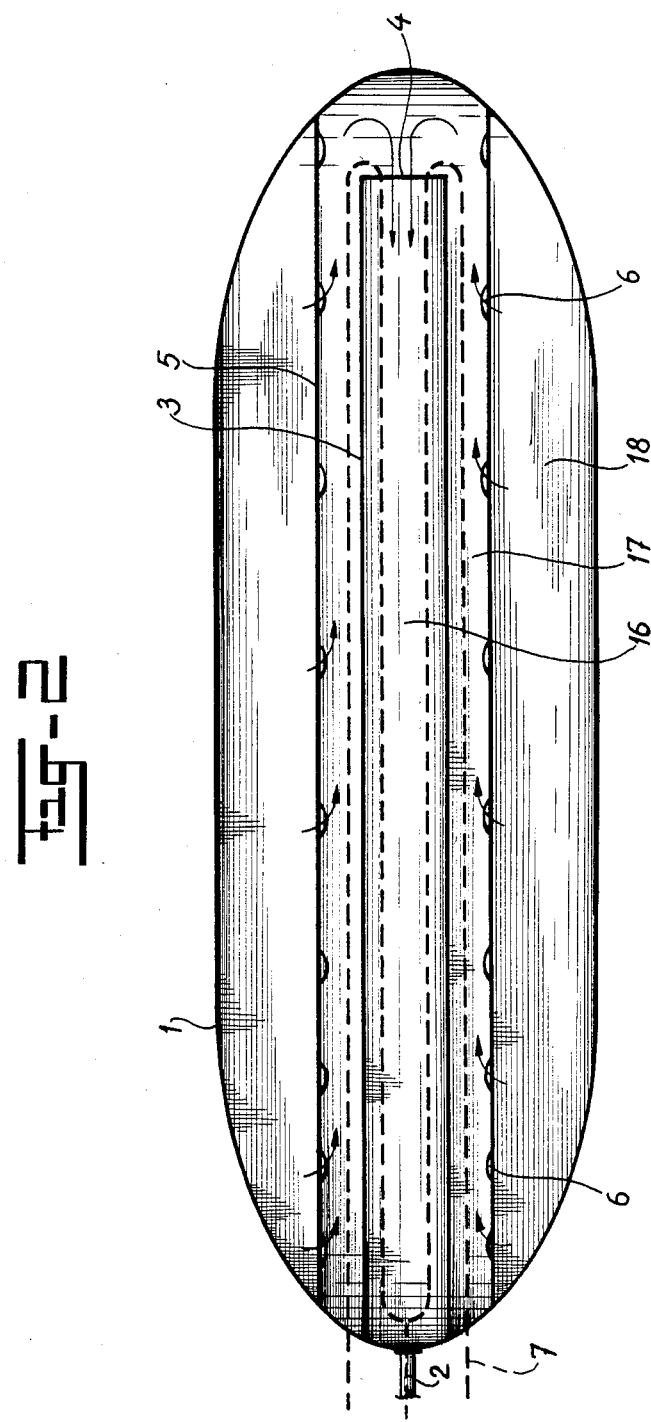
FIG. 2 is a horizontal section through this device along the line II—II in FIG. 1.
Figure 3:
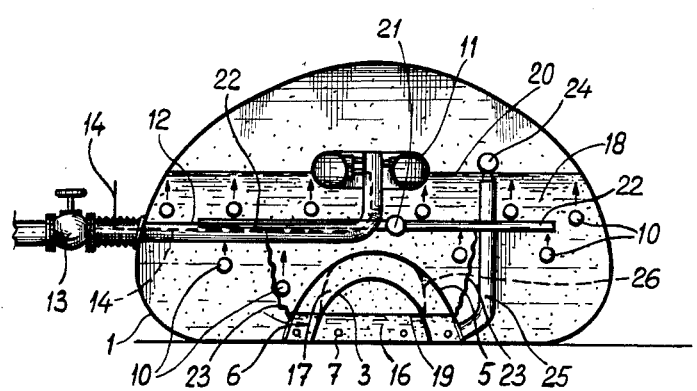
FIG. 3 is a vertical transverse section according to line III—III in FIG. 1.

The device of FIGS. 1 to 3 comprises a wall 1 of flexible material, for instance a nylon fabric, coated with and/or impregnated by a gastight plastic layer, for instance of pvc. Flexible parts of the device which will be described below may also consist entirely or in part of such material. The wall 1 moreover has an external or internal heat insulation not shown, which may be formed by an enveloping blanket of fiberglass wool and/or by an internal and/or external insulating layer adhering to the wall, for instance, consisting of a flexible foam plastic material.

A hose connection 2 with valve and easily operable tube or hose coupling opens in a central plane in the lower part of a short end of the wall. Within said enveloping wall a tunnel wall 3 is provided connected sealingly to the outer wall 1 around the hose connection 2 and connected with its lower edges to the bottom of the device. At its end opposite connection 2, this tunnel wall terminates at a short distance from wall 1 to form an opening 4.

Around said tunnel wall 3 there is, substantially concentrically therewith, a second tunnel wall 5, extending over the entire length of the wall 1 and connected at both ends sealingly thereto, while its lower ends are sealingly connected to the bottom of the device. Said longitudinal lower edges have openings 6 which, as appears from FIGS. 1 and 2, are not uniformly distributed over the length thereof, but at the left give more total opening area than towards the right, which may be obtained by a difference in size of each opening, but which in the drawing is obtained by a difference in mutual distances between the openings.

In FIG. 3, reference 26 indicates that the tunnel wall 3 may be connected to the tunnel wall 5 so that in the central area they form one single roofpart. If the tunnel wall 3 is entirely separate from the tunnel wall 5, as shown by uninterrupted lines in FIGS. 1 and 3, the upper part of tunnel wall 3 may be suspended for instance by wires from the upper or roofpart of tunnel wall 5, so that tunnel wall 3 does not hang down and sink onto the liquid surface if this is lower than the top part of tunnel wall 3.

Below tunnel wall 5 a heating tube 7 is provided, which, as appears from FIG. 2, enters the wall 1 through the wide hose connection 2 to enter the space below the tunnel wall 3, then branches into two tubes or hoses, each leaving this space through opening 4 and which are then bent back to a hairpin curve to extend below tunnel wall 5 outside tunnel wall 3 and so leave the wall at the same side where this tube entered the device.

The space below the upper part of tunnel wall 5 is connected through a gas duct 8 (FIG. 1), in which there is a three-way valve 9, to a header or distributing duct part not shown, connected to a number of flexible hoses 10 extending parallel to the longitudinal direction of the wall 1 and are connected to said wall near both ends. These hoses have openings to discharge gas into the surrounding space.

The three-way valve 9 in one position connects the space below tunnel wall 5 to the outside air or to suitable collecting means not shown, as indicated by 9', in which case the hoses 10 are closed by said valve.

Another possibility is that a single flexible duct 21 is connected to the gas duct 8 (FIG. 3), which duct 8 replaces all ducts 10 or most of them and which serves as an internal distributing duct for the gas. This duct is connected near both ends with the wall 1 and has a number of preferably flexible transverse ducts 22 closed at their ends. In order to keep these sufficiently in place, wires 23 extend between each of said transverse ducts and lower points, preferably points on tunnel wall 5 and said wires may for instance each engage the upper edge of an opening 6 in said wall. Gas discharge openings are provided in said transverse ducts, preferably in the lower part thereof, so that as much gas as possible remains therein to keep this duct system in place by floating if they are embodied as flexible hoses. If there is no gas in these transverse ducts they may hang down, but this is of no harm as they will easily regain the position shown if gas is again introduced therein.

An air tube 11, for instance the inner tube for a car tire, floats on the liquid surface 20 in the device and carries a gas discharge duct 12 guided through the wall 1 to the outside (FIG. 3) and there having a valve 13. The valve 15 of belt 11 (FIG. 1) is connected to a duct 14 for inflating the tube 11 by air under pressure and guided through the thicker duct 12 to the outside. It is thus possible to inflate the tube during operation and to check the air pressure therein.

Another possibility is that the gas is discharged from below tunnel wall 5 not through duct 8 to the outside but through a hose which leads this gas first upward and then through the wider discharge duct 12 to the outside, so that no separate opening through the wall 1 is necessary therefor.

The mounting and operation of this device is as follows: it is imagined that wall 1 extends all around the device so as also to form the bottom thereof. This means that the device may be transported to the site where it has to be used in empty and deflated condition and even folded or wound up into a roll. On the site it may be positioned e.g. on a concrete floor with a heat insulating layer thereon, or in a ditch with gradually sloping walls. By pumping in air this device may be inflated to take up the desired shape about as shown. All connections are now made. If the heating tube 7 is not embodied as a flexible tube it is now mounted, for instance by entering it through openings in the wall 1, which are thereafter adequately sealed and there may be suitable hose or tube couplings near both ends of the wall 1. In this case it may be desired to position only the straight ends of the tubes 7 within the wall 1, all curves, couplings and connections being positioned outside the wall 1. As however the temperature of the heating fluid need not be higher than 55° C., it is very well possible to make the tube 7 flexible and to mount it in the wall 1 when manufacturing the device, so that tube 7 may be folded or wound up together with the other parts of the device. If desired a heat insulating blanket is provided over wall 1.

Liquid to be treated such as liquid manure, being manure diluted by water and if desired having the solid particles therein ground, chopped or cut to much smaller size so that the entire substance behaves substantially as a liquid, is pumped into the device through connection 2. If this substance itself does not have enough methanogenic bacteria, active sludge or an other suitable inoculum may be added. If desired the device is first filled up to about half its volume with a suitable inoculum manure, which may be manure already treaded in such a device previously. Heating fluid is guided through tube 7 to bring the contents at the desired temperature, which in normal operation is for instance 30° C. for the methane fermentation space 18 and for instance about 40° C. for the space for hydrolysis and acidification below wall 5.

Hydrolysis, acidification and methane fermentation now begin to take place, which occurs usually quite rapidly, although it may take several weeks before the process is fully at an effective level. Thereafter further liquid to be treated is added periodically, for instance ten times a day in a quantity which may be such that in several days the entire volume of the space below tunnel wall 5 is replaced. If desired, the course of the process may be promoted by re-introducing gas discharged through duct 12 through supply 2, for instance periodically discharging it and introducing it again, also to promote mixing.

As the feed enters the space below wall 3, this space 16 mainly acts as the space for hydrolysis. Liquid therefrom is displaced to space 17 between tunnel walls 3 and 5, which material is ripe for acidification, which thus takes place mainly in space 17.

During these processes gas is formed, mainly during acidification, and this is mainly carbon dioxyde with some methane. This is collected below the upper part of tunnel wall 5 and it pushes the liquid gradually from space 17 to space 18 to the side thereof and above it, being the methane fermentation space, through the openings 6. If this is continued too long, finally also gas will pass through openings 6, but this phenomenon forms a brake for itself because with increasing gas quantity the liquid below tunnel walls 3 and 5 decreases, so that less gas is generated. Moreover it is strongly recommendable to open the gas valve 9 in gas duct 8 in a further stage, and preferably suddenly and only during the short period. Thereby the gas flows away at 9' or flows to the tubes or hoses 10 or 21, 22, so that it rises as bubbles through the liquid in the methane fermentation space 18. As gas thus leaves the space below tunnel walls 3 and 5, liquid flows back through openings 6 from space 18 to space 17 as shown by arrows in FIG. 2. The uneven distribution of openings 6 over the length of wall 5 has the advantage of a more uniform refreshment of liquid in space 17 as it more easily enters those parts of space 17 which are farther away from opening 4.

The liquid level in tunnels 16 and 17 thus decreases gradually and then rises suddenly by said sudden gas discharge. This gas discharge may be controlled by measuring the height of liquid level 19 so that each time this reaches a certain height when moving downwardly, a signal is given to open valve 9 during a short period. It is also possible to have time switching means to open said gas discharge according to a predetermined time pattern.

The openings in the hoses or tubes 10 may be provided at distances of for instance 50 cm from each other and may have a diameter of for instance about 8 mm. They may be provided at the lower side of said hoses or tubes, so that less liquid enters these tubes if they do not discharge gas and so that the gas will rise as bubbles both to the left and to the right along said ducts.

In the methane fermentation space 18 gas is formed, mainly methane, and all the gas collects in the upper part of the device below wall 1 above liquid level 20. It is possible to discharge this gas continually, preferably at a suitable pressure adapted for further use without compression, through duct 12. If gas generation is at a too low level, the discharge may be stopped or decreased.

It is possible in many different ways to measure said gas quantity or the height of liquid level 20, for instance with known feelers with switches. In the known embodiment, if there is far too little gas, the upper part of wall 1 may sag down onto airtube 11, which thereby will be submerged further and will thus generate an increase of internal pressure, which may be observed by air pressure measurement through signal duct 14.

By a discharge opening 27, treated manure or the like may be discharged from the device at intervals, for instance together with or shortly before or after the introduction of new liquid to be treated, continuously or at any desired moment. It is also possible to apply an automatically operating overflow or weir system with a standpipe, for instance a hose connected to a pole outside the device, extending to such a height that the desired pressure in the device is maintained. The treated liquid discharged may be spread over meadows.

There may also be a discharge connection at the lower part of wall 1 to discharge settled material from time to time.

As the gas discharge 12 leaves the wall 1 below the liquid level 20, there is less risk of gas leakage, while liquid leakage can easily be observed.

It is often advantageous to lead gas from below the top part of wall 1 alternatively into methane fermentation space 18 (so in hoses 10 or 21, 22) and to the outside (through for instance 9') so that each desired amount of stirring in the methane fermentation space 18 and/or discharge of carbon dioxide to the outside may be chosen.

In FIGS. 1 and 3 a ball or similar float 24 has been shown, which has wires to support a hose 25 which opens at its lower end in an opening 6 of tunnel wall 5 between the opening 4 and the adjacent the shorter portion of wall 1, at the right in FIG. 1. The hose 25 has its open upper end at a short distance below float 24. Thereby, if gas is discharged from the space below tunnel wall 5, the liquid is as it were sucked through openings 6 to said space and thereby also a part of the layer floating on the liquid in space 18 is sucked into hose 25 and fed to the acidification space 17, so that said floating layer is disturbed and broken up and the material therein is treated again to be broken down more fully.

All kinds of measuring, control and signal ducts may be applied if desired. They may be quided at least for the greater part through openings already there for other purposes, for instance through duct 12, so that in wall 1 the smallest possible number of openings is necessary.

Figure 4:
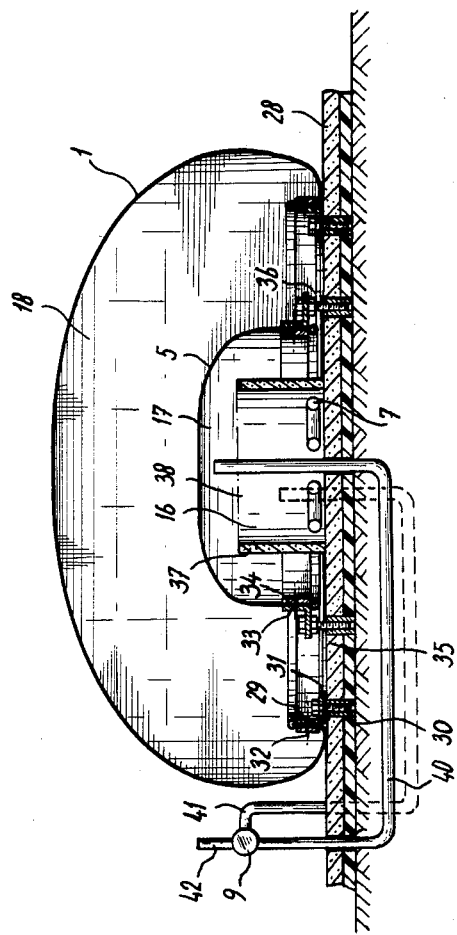
FIG. 4 gives in somewhat less detail a transverse section the same as FIG. 3, but through such a device in a somewhat different embodiment.
Figure 5:
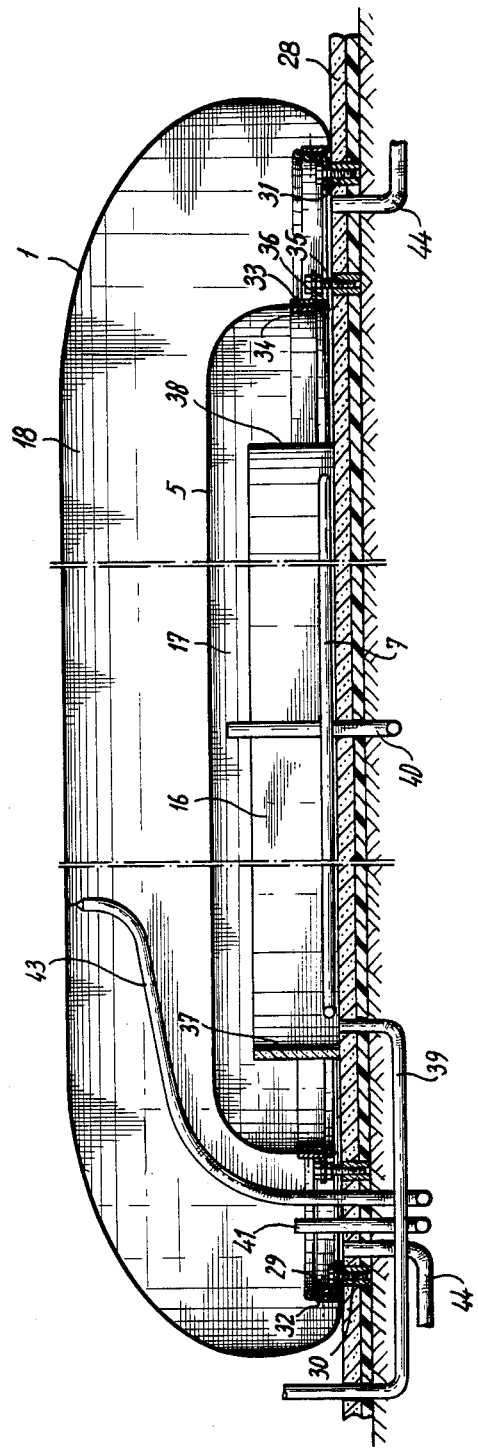
FIG. 5 gives a longitudinal section comparable to FIG. 1, but of the device of FIG. 4.

In FIGS. 4 and 5 the device does not have a flexible wall entirely enclosing the space within it, but the flexible wall 1 is connected all around to a concrete floor slab 28, for which purpose a rectangular angle iron beam frame 29 is connected thereto, e.g. by studs 30 embedded in the concrete thereof. This concrete slab 28 may reset on a heat insulating layer, e.g. of fibrous mineral material, not shown.

Between the beam frame 29 and the floor slab 28 there may be a layer 31 of resilient sealing material such as rubber. By nuts screwed onto the studs 30, the frame 29 is secured to the floor slab 28. The flexible wall is clamped between the upstanding leg of the angle iron of frame 29 and a strip 32 by bolts and nuts drawing these parts together.

The tunnel wall 5 for defining an acidifying space 17 below it is also of flexible gas tight material and is clamped between an angle iron frame 33 and a strip 34, but frame 33, supported by studs 35 in the concrete floor and nuts screwed thereon both on top of and below the horizontal flange of angle irons 33, is supported at a short distance above the conrete floor so as to leave an opening 36 all around wall 5, replacing the discrete openings 6 of FIGS. 1 to 3. If desired, this opening may be absent in parts of the periphery of wall 5, e.g. at the right in FIG. 5 opposite opening 38 to be described.

On the concrete floor slab 28 there is a concrete or brick wall 37, defining a hydrolysis space 16 open in its top face. It consists of three wall parts together forming a U-shape as seen from above, there being between two long parallel wall parts parallel to the longitudinal axis of the device a short connecting wall part at one end, at the left in FIG. 5. At the right, there is no such wall part, so that a free opening 38 is formed. The liquid to be treated is supplied through a duct passing underneath the bottom and through the concrete slab 28, opening at 39 in the bottom of space 16 near said short connecting wall (FIG. 5). One or more gas ducts 40 open at a short distance below tunnel wall 5 and lead through the bottom to the outside, where a three-way valve 9 is provided thereon, giving access at will to a duct 41 or to the ambient atmosphere or an outside collecting source through connection 42. Duct 41 (of which there may also be more than one) passes through the bottom to open between walls 1 and 5 (FIG. 5). If desired, the parts of ducts 40 and 41 above the slab 28 may entirely or in part consist of flexible hoses suspended e.g. by a wire from the wall 1 or 5 respectively above it. Heating tubes 7 are present near the bottom within the walls 37 and if desired they may also extend along the outside of such walls within the outer boundary of wall 5 or even outside thereof below wall 1.

The operation of this device will not need much description as it is in essence the same as that of the device of FIGS. 1 to 3. As soon as so much gas has collected below wall 5 that the liquid level in spaces 16 and 17 is below the top of wall 37, spaces 16 and 17 are separated entirely apart from the connection at 38. The opening 36 below the lower edge of wall 5 allows the gas below said wall to push the liquid into space 18 and, if gas is suddenly discharged through duct 40 and valve 9, to allow the liquid from space 18 to return in part to the space below wall 5 for good mixing and profound treatment as described.

A hose 43 may be suspended, e.g. by a wire, from the roof of wall 1 near the center, or there may be several of such hoses. They lead to one or more ducts through the slab 28 to a suitable outside valve not shown and from there to suitable means for treating and using the methane gas.

The supply pipe 41 for the gas fed to valve 9 from below wall 5 is here shown as simply opening upwardly in space 18 and as not having distributing means to distribute this gas below the level of the liquid over almost the entire surface of space 18 as in FIGS. 1-3, where this is done for good temporary mixing and breaking up of a scum layer on the liquid, but this is not always necessary, so that it is not provided for in the device of FIGS. 4 and 5.

One or more rather wide discharge ducts 44 (two being shown in FIG. 5) pass through slab 28 and to an outside valve not shown and open at the top level of this slab in space 18 to remove sludge and any settled substances periodically.

These devices may have further control means not shown. For controlling gas discharge and liquid levels there may be used all kinds of suitable sensors, such as floats suspended by a wire from the roof and tilting when the liquid level has risen sufficiently, said tilting operating e.g. an electric switch or other switching means.

I claim:

1. In an apparatus for digesting organic waste feed mix by first acidifying and then fermenting the acidified material to produce methane gas, the combination comprising:

an outer digestion enclosure with partition means secured therein defining an inner enclosure,
said inner enclosure dividing said digestion apparatus to define a methane fermentation chamber located between said outer and inner enclosures and being constructed and arranged to form an acidification chamber adjacent to said fermentation chamber,
said inner enclosure projecting upwardly toward the upper portion of said digestion enclosure to define a top collecting wall of said acidification chamber, said enclosures being made of substantially gas tight material,
means for providing a substantially liquid organic waste mix to said acidification chamber wherein said mix is acidified thereby producing a gas,
aperture means located at a first level substantially lower than the uppermost portion of said collecting wall communicating said acidification chamber with said methane fermentation chamber,
said methane fermentation chamber being configured to accumulate liquid to a second level higher than the level of said aperture means so that said aperture means are submerged,
the gas generated in said acidification chamber being entrapped and accumulated by said collecting wall of said acidification chamber so as to cause an increase in pressure and force acidified mix from said acidification chamber through said aperture means to said fermentation chamber against the head of liquid accumulated in said methane ferementation chamber above said aperture means, outlet means for withdrawing liquid from said fermentation chamber, and means for withdrawing gas from said fermentation chamber.

2. The combination according to claim 1 further comprising gas duct means and a three-way valve, said gas duct means and said three-way valve being constructed and arranged to selectively couple said acidification chamber and said methane fermentation chamber in a first valve switching position and to vent said acidification chamber to the exterior of said outer digestion enclosure in a second valve switching position.

3. The combination according to claim 2, wherein said gas duct means comprise a plurality of tubes each of which includes a plurality of gas discharge openings communicating with said methane fermentation chamber.

4. The combination according to claim 1, wherein said outer digestion enclosure and said partition means are formed of a flexible gastight material.

5. The combination according to claim 4, wherein said methane fermentation chamber is provided with a heat insulating layer.

6. The combination according to claim 1, further comprising pressure balancing line means connecting said acidification chamber and said methane fermentation chamber, said pressure balance line means including a hose attached to flotation means disposed in said fermentation chamber and arranged thereon so that its end is maintained at a level slightly below the liquid level in said methane fermentation chamber.

7. The combination according to claim 1, wherein said means for withdrawing gas from said fermentation chamber include a flexible duct attached to float means in such a manner as to maintain an opening of said duct above the liquid level in said fermentation chamber.

8. The combination according to claim 7, wherein said float comprises an inner tube provided with an inflating tube extending to the exterior of said enclosure.

9. In an apparatus for digesting organic waste material by a sequence of first hydrolysis, second acidification, and third fermentation to produce methane gas, the combination comprising a digestion enclosure with domed partition means secured thereto for dividing said enclosure into an acidification tunnel and an elongated fermentation chamber adjacent thereto, said partition means being constructed and arranged to project upwardly toward an upper wall of said enclosure so that it forms an arcuate top collecting wall of said acidification tunnel whereby said acidification tunnel is disposed at a level below said fermentation chamber which extends concentrically thereabout, aperture means for coupling said fermentation chamber and said acidification tunnel arranged at a level substantially below the uppermost portion of said arcuate collecting wall, separation means for defining a hydrolyis zone within said tunnel positioned, configured and dimensioned so that said hydrolysis zone is at a level substantially lower than the uppermost portion of said arcuate collecting wall and communicates with said acidification chamber and means for providing an organic waste feed mix to said hydrolysis zone wherein said feed mix undergoes hydrolysis to reduce its solid content and then flows into said acidification chamber as substantially liquid organic waste material and is acidified therein to produce a gas, said gas being entrapped and accumulated by said arcuate collecting wall of said acidification chamber to increase in pressure thereby forcing said acidified organic waste mix through said aperture means to said fermentation chamber, outlet means for withdrawing liquid from said fermentation chamber and means for withdrawing gas from said fermentation chamber.

10. The combination according to claim 9, wherein said separation means comprises a rigid wall with two oblong parallel sides and a connecting wall arranged to form a U-shaped compartment.

* * * * *